(12) United States Patent
Markussen

(10) Patent No.: US 9,242,044 B2
(45) Date of Patent: Jan. 26, 2016

(54) AUTOMATIC INJECTION DEVICE

(75) Inventor: Tom Hede Markussen, Bagsværd (DK)

(73) Assignee: Novo Nordisk A/S, Bagsvaerd (DK)

( * ) Notice: Subject to any disclaimer, the term of this patent is extended or adjusted under 35 U.S.C. 154(b) by 736 days.

(21) Appl. No.: 12/665,988

(22) PCT Filed: Jul. 3, 2008

(86) PCT No.: PCT/EP2008/058606
§ 371 (c)(1),
(2), (4) Date: Jun. 30, 2010

(87) PCT Pub. No.: WO2009/007305
PCT Pub. Date: Jan. 15, 2009

(65) Prior Publication Data
US 2010/0280460 A1    Nov. 4, 2010

Related U.S. Application Data

(60) Provisional application No. 60/952,275, filed on Jul. 27, 2007.

(30) Foreign Application Priority Data

Jul. 6, 2007   (EP) ..................................... 07111968

(51) Int. Cl.
*A61M 5/32*    (2006.01)
*A61M 5/20*    (2006.01)
*A61M 5/24*    (2006.01)
*A61M 5/315*   (2006.01)

(52) U.S. Cl.
CPC ............. *A61M 5/2033* (2013.01); *A61M 5/322* (2013.01); *A61M 5/3232* (2013.01); *A61M 5/3234* (2013.01); *A61M 5/2466* (2013.01); *A61M 5/31583* (2013.01); *A61M 5/3202* (2013.01); *A61M 5/326* (2013.01); *A61M 2005/206* (2013.01); *A61M 2005/2086* (2013.01)

(58) Field of Classification Search
CPC .......... A61M 5/322; A61M 2005/206; A61M 2005/2086; A61M 5/2033; A61M 5/3232; A61M 5/3234
See application file for complete search history.

(56) References Cited

U.S. PATENT DOCUMENTS

| 5,320,609 | A | * | 6/1994 | Haber et al. | 604/135 |
| 5,487,732 | A | | 1/1996 | Jeffrey | |
| 5,779,677 | A | * | 7/1998 | Frezza | 604/134 |
| 5,865,804 | A | | 2/1999 | Bachynsky | |
| 5,957,897 | A | | 9/1999 | Jeffrey | |
| 2002/0095120 | A1 | * | 7/2002 | Larsen et al. | 604/187 |
| 2003/0144633 | A1 | * | 7/2003 | Kirchhofer | 604/201 |
| 2009/0048561 | A1 | * | 2/2009 | Burren et al. | 604/135 |

FOREIGN PATENT DOCUMENTS

| EP | 0 516 473 | 2/1992 |
| EP | 754469 | 1/1997 |
| JP | 2003-088585 A | 3/2003 |

(Continued)

*Primary Examiner* — Nathan R Price
*Assistant Examiner* — Anh Bui
(74) *Attorney, Agent, or Firm* — Wesley Nicolas

(57) ABSTRACT

An automatic injection device (100) adapted to automatically eject a dose of a medicament by automatically inserting a needle (112) into the skin of a user, ejecting a dose of a medicament through the needle, and subsequently retracting the needle into a housing (122) of the device.

18 Claims, 10 Drawing Sheets

(56) References Cited

FOREIGN PATENT DOCUMENTS

| WO | WO 99/07425 | 2/1999 |
| WO | WO 00/56384 | 9/2000 |
| WO | WO 00/69488 | 11/2000 |
| WO | WO 02/17996 | 3/2002 |
| WO | 2007006662 A1 | 1/2007 |
| WO | 2007/017052 A1 | 2/2007 |

* cited by examiner

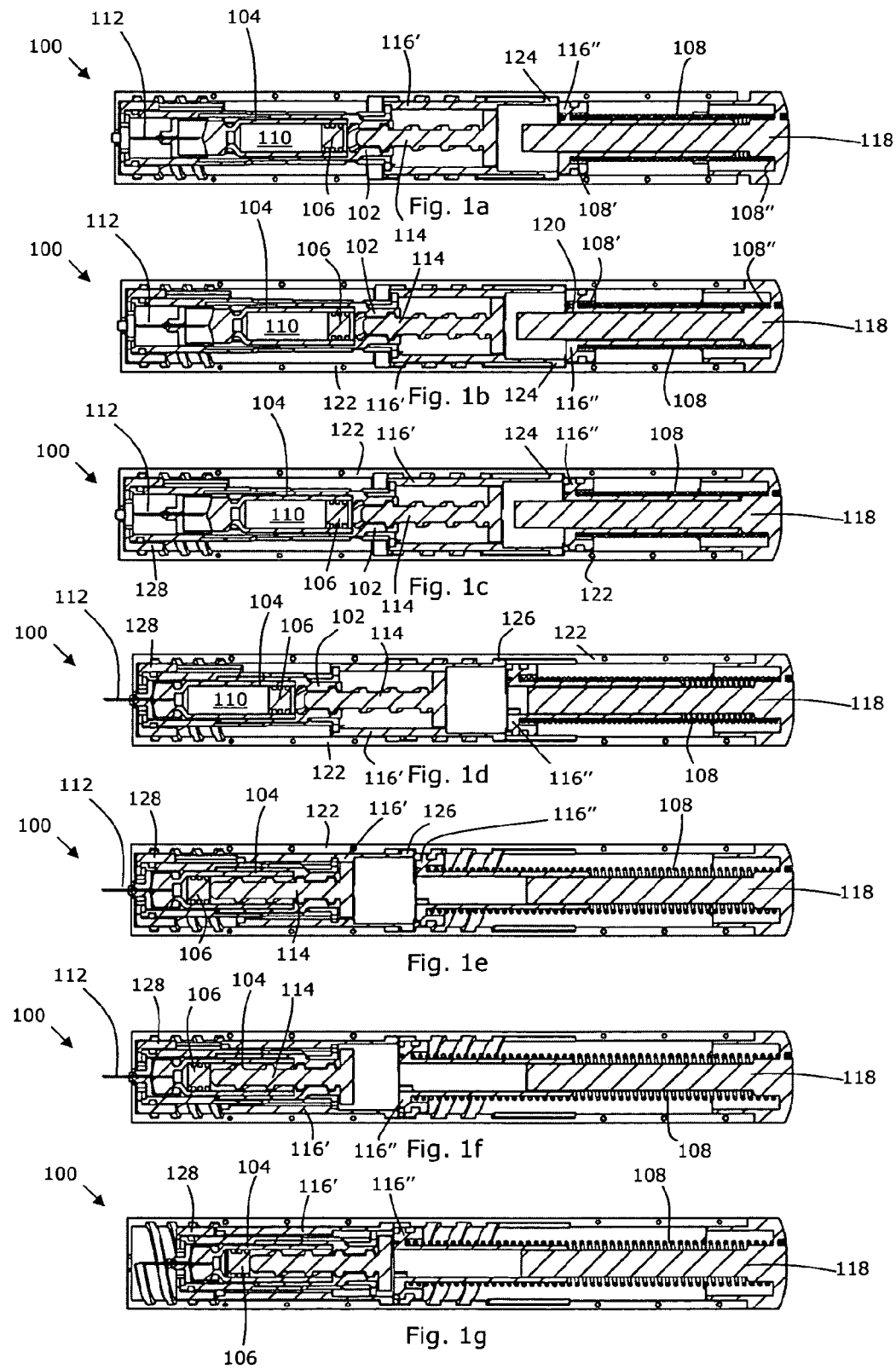

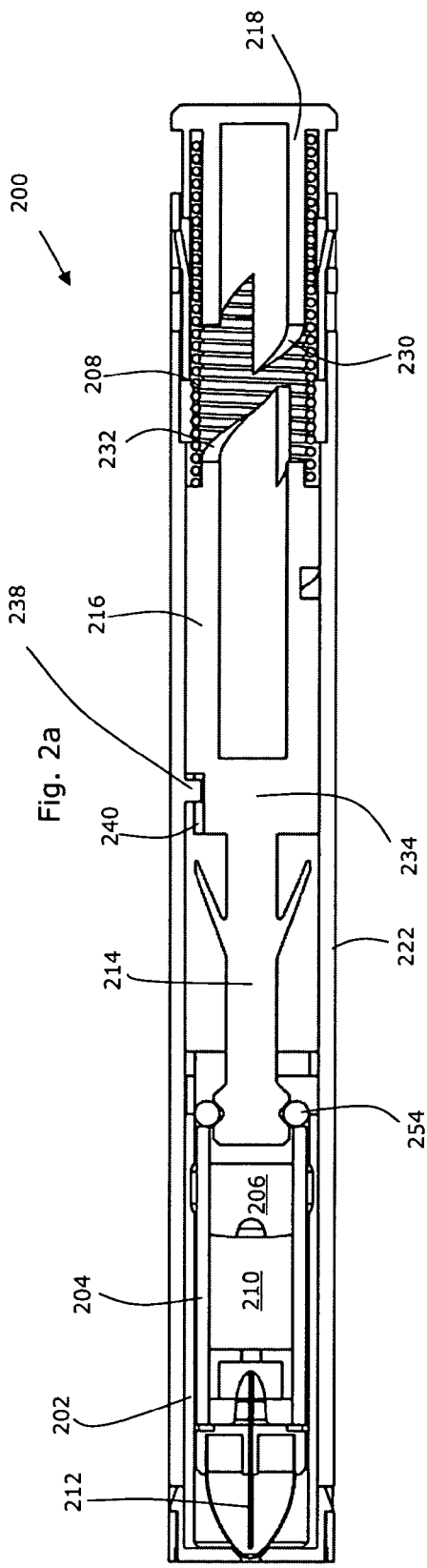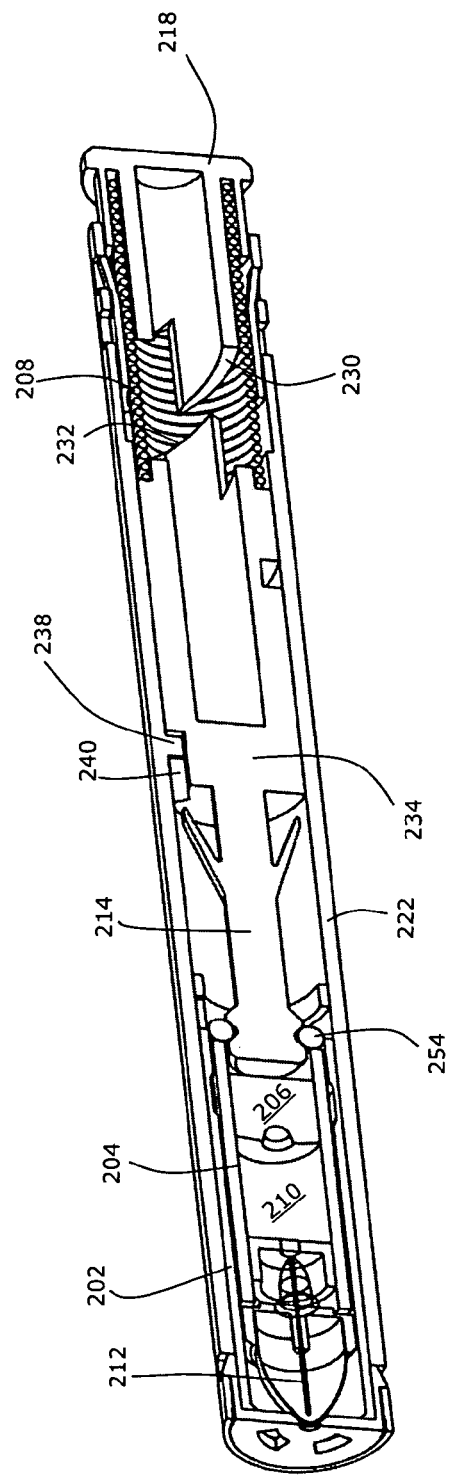
Fig. 2a
Fig. 2b

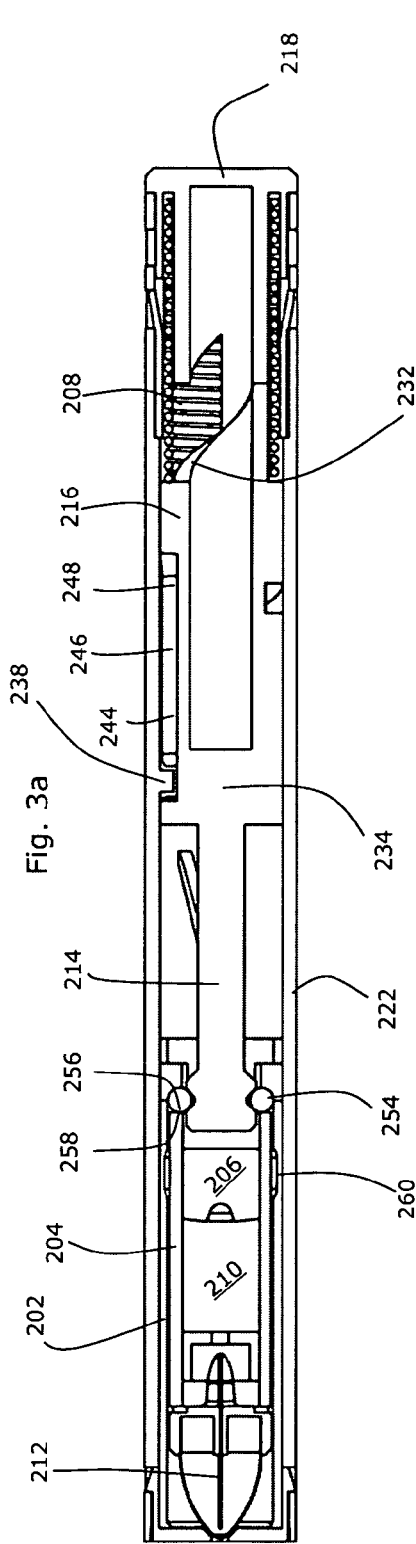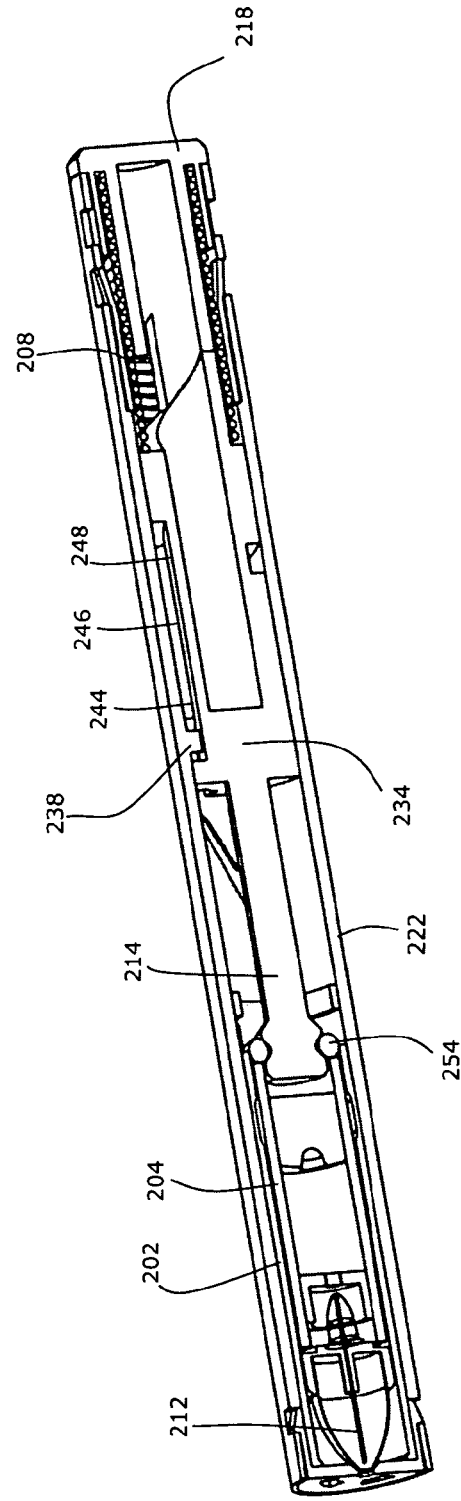

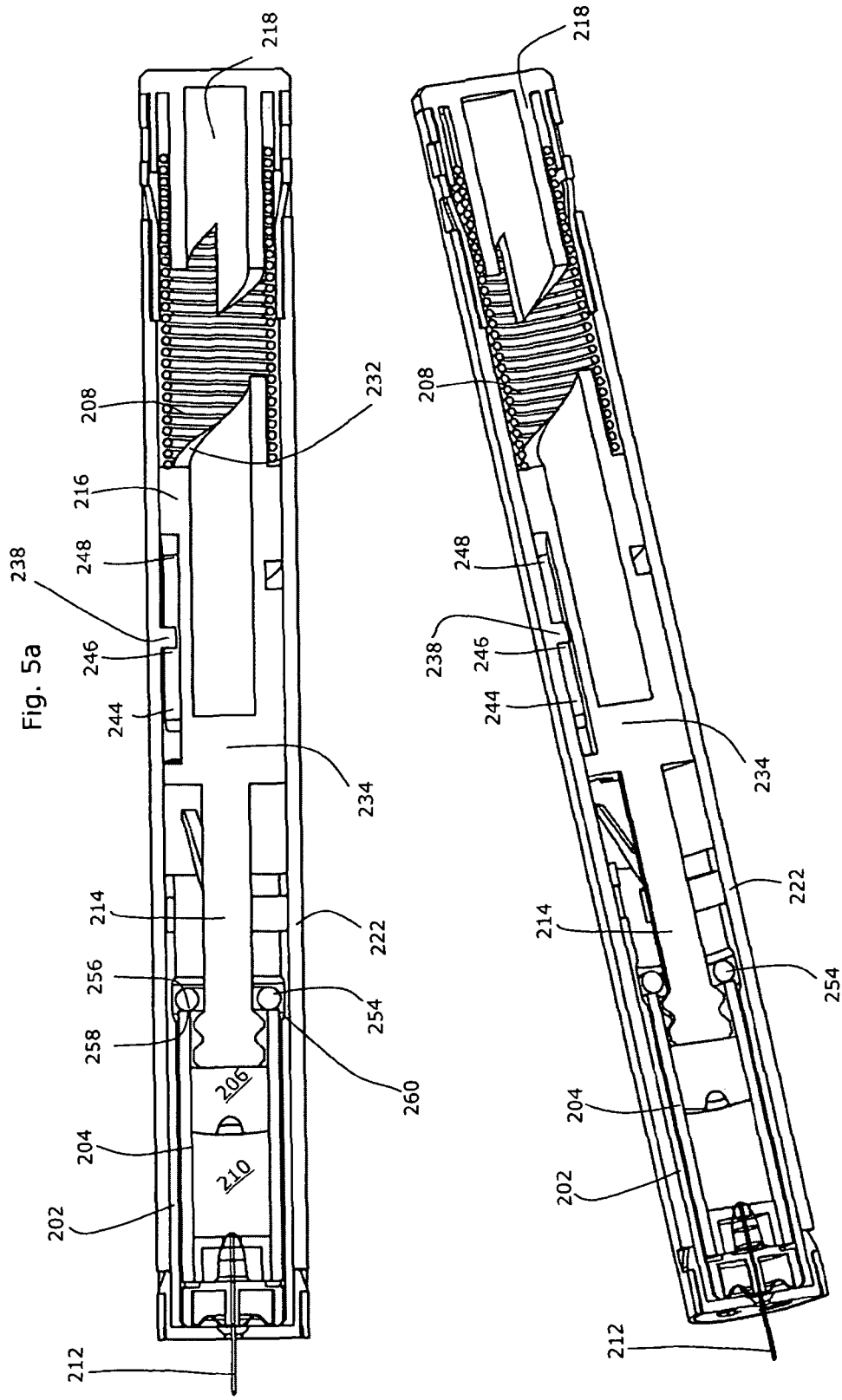

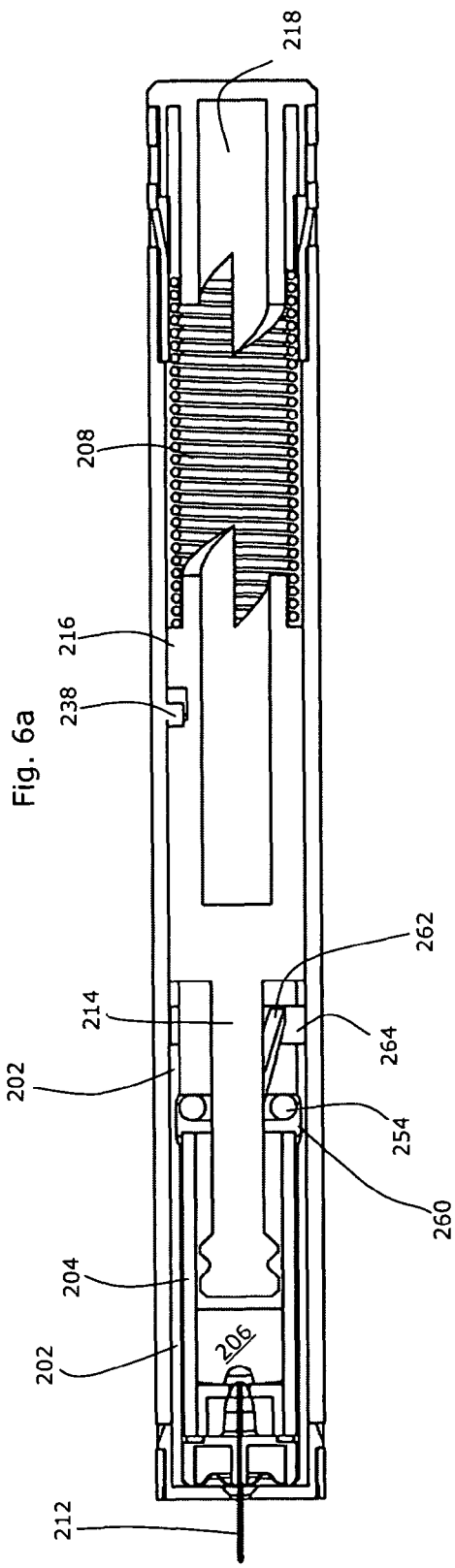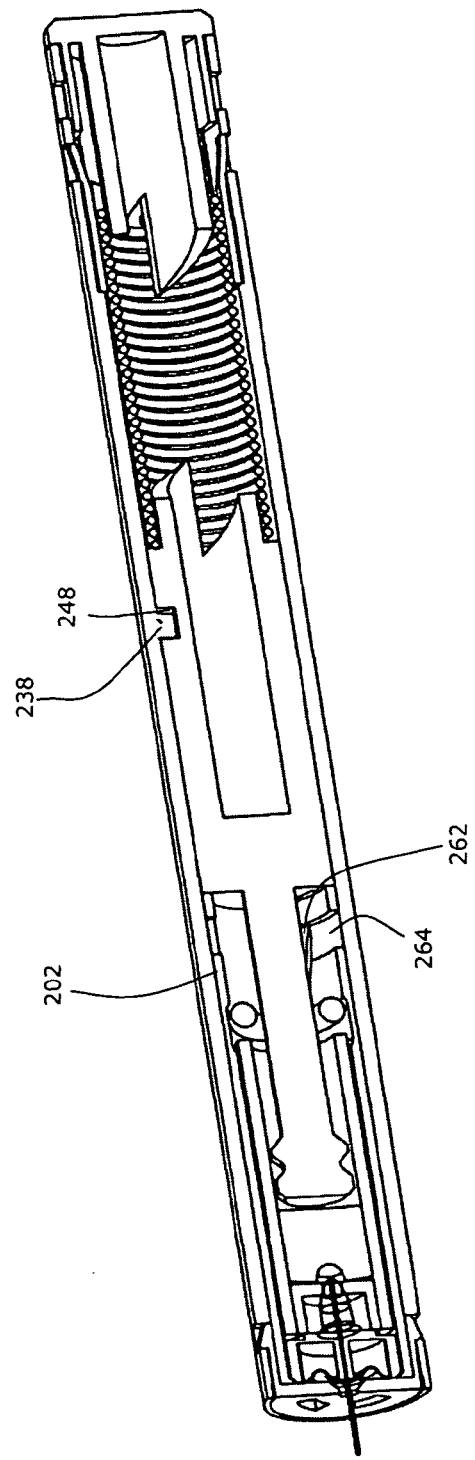
Fig. 6a
Fig. 6b

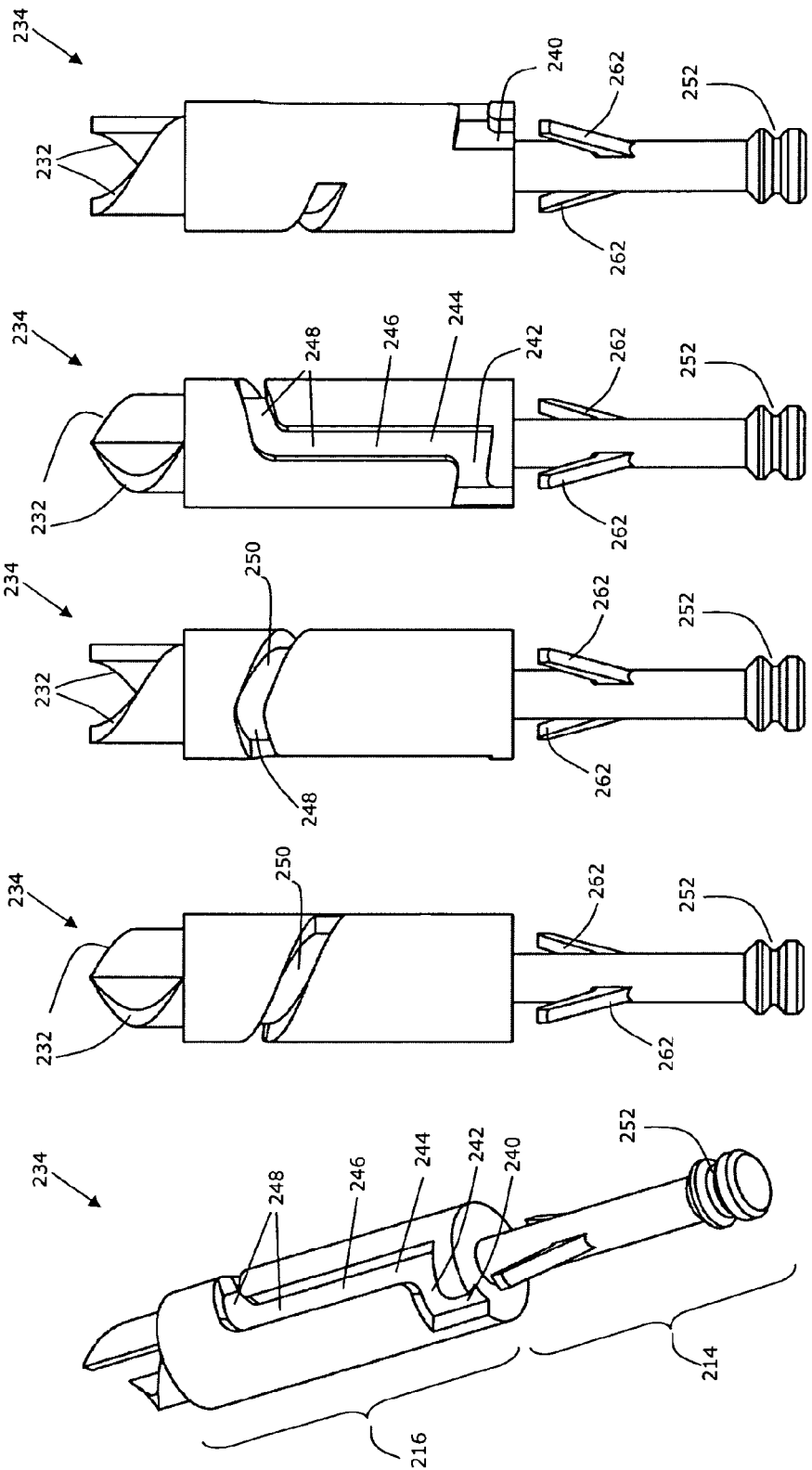

AUTOMATIC INJECTION DEVICE

CROSS-REFERENCE TO RELATED APPLICATIONS

This application is a 35 U.S.C. §371 national stage application of International Patent Application PCT/EP2008/058606 (published as WO 2009/007305), filed Jul. 3, 2008, which claimed priority of European Patent Application 07111968.9, filed Jul. 6, 2007; this application further claims priority under 35 U.S.C. §119 of U.S. Provisional Application 60/952,275, filed Jul. 27, 2007.

FIELD OF THE INVENTION

The present invention relates to an automatic injection device adapted to automatically eject a dose of a medicament by automatically inserting a needle into the skin of a user, ejecting a dose of a medicament through the needle, and subsequently retracting the needle into a housing of the device.

BACKGROUND OF THE INVENTION

In relation to some diseases patients must inject a medicament on a regular basis such as a plurality of times each day. In order to help patients overcome fear of needles, fully automatic injection devices have been developed that makes the use of an injection device as simple as possible. Such devices are designed such that a user shall position the injection device onto his skin and manipulate an activation button. Such activation causes the device to insert a needle into the skin, eject a dose of the medicament and subsequently retract the needle into a housing of the device.

WO 02/17996 discloses an automatic injection device which automatically injects a pre-measured quantity of fluid medicine when it is released. The tensing spring moves the ampoule and the injection needle from a storage position to a deployed position and ejects the medicament through a linear movement.

It is an object of a preferred embodiment of the present invention to provide an alternative to known devices for automatically injecting a medicament. Moreover, it is an object of a preferred embodiment of the present invention to provide an automatic injection device allowing dosing of the medicament with a high precision volume. Furthermore, it is an object of a preferred embodiment to provide the user with a tactile, visible or auditive indication of the point in time wherein the ejection process has terminated.

DESCRIPTION OF THE INVENTION

The present invention relates to an automatic injection device comprising:
 a housing;
 an ampoule holder for accommodation of an ampoule having a piston slidably arranged therein, the ampoule and the piston defining a reservoir for accommodation of a medicament;
 a piston rod arranged such with respect to the ampoule holder that for a first set of relative positions between the ampoule holder and the piston rod, rotation of the piston rod causes the piston to be moved in a distal direction relative to the ampoule holder whereby a first part of the medicament is expelled;
 a resilient element adapted to:
  move the ampoule holder into a deployed position by moving the ampoule holder in the distal direction relative to the housing, and subsequently
  rotate the piston rod relative to the ampoule holder when the ampoule holder and the piston rod are positioned in the first set of relative positions whereby the first part of the medicament is expelled from the ampoule; and subsequently
  retract the ampoule holder away from the deployed position by moving the ampoule holder in a proximal direction relative to the housing.

In one embodiment the injection device comprises an injection button allowing a user to initiate the injection process by pressing the button in the distal direction. Upon such movement in the distal direction, the pre-strained resilient element is released from a locked state into an unlocked state wherein the resilient element is free to move the ampoule holder into the deployed position and to rotate the piston rod relative to the ampoule holder. The injection button may define the proximal end of the device e.g. such that the button is arranged to be activated by means of a thump of the user. Alternatively, the injection button may be provided on an outer surface along the length of the injection device, e.g. such that the button is arranged to be activated by an index finger of the user.

The injection device comprises a housing which may define an outer surface of the injection device. The housing may define a cylindrical element defining a cavity for accommodation of at least one of the ampoule, the ampoule holder, the resilient element, the means for retracting the ampoule holder and a needle.

At least a part of the ampoule may be cylindrical and adapted to receive the piston. The piston may be slidably arranged inside the ampoule so as to be movable from a proximal position into a distal position. In one embodiment, the volume of the reservoir is smaller when the piston is positioned in the distal position than when the piston is positioned in the proximal position.

In order to allow the piston to be moved from the proximal to the distal position, the device comprises a piston rod. The piston rod may be arranged such with respect to the ampoule holder that rotation of the piston rod causes the piston to be moved in a distal direction relative to the ampoule holder whereby the medicament is expelled. In a first embodiment, said rotation of the piston rod is relative to the ampoule holder. In a second embodiment, said rotation of the piston rod is relative to the housing of the injection device.

In one embodiment the piston rod and the ampoule holder define mating threads so as to allow the piston rod to be threadedly received in the piston holder. Accordingly, the ampoule holder may define a passage having a threaded inner surface and the piston rod may have a threaded outer surface.

In another embodiment, the piston rod is threadedly received in the housing e.g. by engagement between a thread defined on an outer surface of the piston rod and a mating thread defined on an inner surface of the housing.

The injection device comprises a resilient element for providing energy to perform the automated injection process. In one embodiment, the resilient element comprises a torsional spring, which may be prestrained rotationally and/or translationally so as to store potentional energy in the automatic injection device.

In one embodiment, the spring/resilient element is provided in a prestrained configuration upon delivery of the injection device to the user. In another embodiment, the spring/resilient element is provided in a non-strained configuration upon delivery of the injection device to the user. In the latter embodiment, the injection device may comprise means for straining the spring. As an example the injection button may be adapted to strain the spring upon rotation of the button in a predetermined direction relative to the housing.

The injection device may comprise means for retaining the spring in the (pre)strained state. Said means may be adapted to be moved into a non-retaining position in which the spring/resilient element is free to be unstrained rotationally and/or translationally. The means for retaining the spring in the strained state may be coupled to the injection button such that movement of the button e.g. in the distal direction, causes the means to be moved in the non-retaining position.

During unstraining of the spring/resilient element, the spring/resilient element is adapted to move the ampoule holder from an initial (proximal) position into a deployed (distal) position by moving the ampoule holder in a distal direction relative to the housing. In one embodiment, movement of the ampoule holder in the distal direction additionally causes the piston rod to be moved in the distal direction such as by the same distance as the ampoule holder. During the movement from the initial into the deployed position, the piston rod may be locked for rotation relative to the ampoule holder whereby the spring is prevented from causing the medicament from being ejected.

In another embodiment, the piston rod is locked for translational movement in a first relative direction relative to the ampoule holder (such as relative towards each other) during movement of the ampoule holder into its deployed position. In fact, the piston rod may in one embodiment abut the ampoule holder such that movement of the piston rod in the distal direction causes the ampoule holder to be moved by the same distance in the distal direction. In one embodiment, the piston rod is locked for rotation relative to the housing during movement of the piston rod from the initial into the deployed position.

In one embodiment, movement of the ampoule holder from the initial to the deployed position causes a needle to be fluidly connected to the reservoir of the ampoule. The needle may comprise a proximally extending needle end with a cutting edge which during said movement perforates a piercable septum/membrane of the ampoule. Said septum may be provided in a distal end of the ampoule.

Furthermore, said movement from the initial into the deployed position may cause a distally extending needle end of the needle to be inserted in to the skin of a user when the distal end of the injection device is positioned adjacent to the skin of the user. In one embodiment, the distally extending needle end is inserted into the skin of the user subsequently to fluidly connecting the needle to the ampoule. In another embodiment, the order is reversed. In yet another embodiment the two acts are preformed substantially concurrently.

In one embodiment, the needle assembly comprises a distal and/or proximal piercable membrane arranged to provide an air (and bacteria) tight seal abound the distally and the proximally extending needle ends, respectively, prior to operation of the injection device.

In the deployed position, the piston rod may be rotationally unlocked relative to the ampoule holder such that the strained spring/resilient element may cause the piston to be moved in the distal direction by rotating the piston rod relative to the housing. In the deployed position movement of the piston rod in the distal direction causes a medicament contained in the reservoir to be expelled through the needle.

In one embodiment, the piston rod is translationally unlocked relative to the ampoule holder when positioned in the deployed position, such that further translational movement of the piston rod in the distal direction causes the piston to be moved in the distal direction, whereby the a part of the medicament is expelled.

In order to retract the needle from the tissue of the user, the injection device may comprise means for moving the ampoule holder away from the deployed position by moving the ampoule holder in the proximal direction relative to the housing. The spring may be arranged to perform said movement subsequent to rotating the piston rod relative to the ampoule holder.

In one embodiment, the ampoule holder is rotationally locked relative to a nut when positioned in deployed position, such as by means of a tongue and groove arrangement allowing the nut and the ampoule holder to be moved translationally relative to each other while being locked for relative rotation. In one embodiment, the ampoule holder is locked for translational movement in the distal direction relative to the nut, whereby movement of the nut in the proximal direction causes the ampoule holder to be moved in the same direction.

In order to retract the needle by moving the ampoule holder in the proximal direction, the nut may be arranged such with respect to the housing, that rotation of the nut relative to the housing causes the nut and the ampoule holder to be moved in the proximal direction relative to the housing.

In one embodiment, the nut is moved in the proximal direction by rotating the nut in the same direction relative to the housing, as the piston rod is rotated relative to the ampoule holder in order to expel a dose of the medicament. Accordingly in a first embodiment, the piston rod is rotated clockwise relative to the ampoule holder—when sees from the proximal end towards the distal end—in order to expel a dose of the medicament and the nut is also rotated clockwise relative to the housing—when sees from the proximal end towards the distal end—in order to retract the ampoule holder away from the deployed position by moving it in the proximal direction. It will be appreciated, that in another embodiment said clockwise rotations may be reversed such that the piston rod and the nut are rotated counter-clockwise in order to expel and retract, respectively.

Just like the piston rod may engage the ampoule holder via a threaded engagement, the nut may engage the housing via a threaded engagement. In order to achieve the aforementioned distal movement of the piston rod, relative to the ampoule holder, and the aforementioned proximal movement of the nut, relative to the housing, the direction of the two threads may be reversed. Accordingly, the thread between the piston rod and the ampoule holder may form a right-hand thread while at the same time the thread between the nut and the housing forms a left-hand thread, or vice versa.

As the piston rod and the nut may be adapted to be moved in the same rotational direction in order to achieve movement in opposite directions, the spring/resilient element may be used to achieve said movements in opposite directions.

In one embodiment, the medical device comprises a driver which is coupled to a distal end of the spring, whereby rotational unstraining of the spring causes the driver to rotate. The driver may be locked for rotation relative to the piston rod, when the ampoule holder is moved into the deployed position, whereby rotational unstraining of the spring causes the driver to rotate the piston rod such that it is moved in the distal direction. During said rotational movement of the piston rod, the driver may move in the distal direction due to a threaded engagement between the outer surface of the driver and a threaded inner surface of the housing.

Said thread between the driver and the housing may be adapted to halt rotation of the driver, when a dose of the medicament is expelled, while allowing translational movement of the driver from the halted position into a position wherein the driver engages the nut. Said translational movement may be achieved by translational unstraining of the spring.

In the position wherein the driver engages the nut, said two elements may be locked for rotational movement while allowing relative translational movement. Accordingly, further rotational movement of the driver relative to the housing may cause the nut to rotate whereby the nut is moved in the proximal direction due to the aforementioned threaded engagement between the nut and the housing.

In view of the above, a first end of the spring may be coupled to an injection button for initiating the injection process and a second end may coupled to a driver which during said injection process may be locked for rotation relative to the piston rod such that rotation of the driver causes the piston rod to rotate.

In order to move the ampoule holder into the deployed position, the driver may be displaceable between a proximal and a distal position relative to the housing, such that when the driver is positioned in the distal position, the ampoule is positioned in the deployed position. Moreover, the driver may be rotatable relative to the housing when positioned in the distal position and locked for rotation relative to the housing in a zone extending from the proximal position and towards the distal position. In one embodiment, the zone corresponds to 90 percent of the distance between the proximal and the distal position, such as 80 percent, such as 70 percent, such as 60 percent, or such as 50 percent.

One advantage of locking the driver for rotation relative to the housing in the aforementioned zone is that a rotationally and translationally strained spring may be used to move the ampoule holder into the deployed position while maintaining the spring in rotationally strained state. Accordingly, the spring may in one embodiment be prestrained translationally and rotationally and arranged such that upon movement of the injection bottom in the distal direction, the spring forces the driver translationally from the proximal position into the distal position in which the rotationally prestrained spring causes the driver to rotate the piston rod, whereby a dose of the medicament is expelled.

In one embodiment, the injection device comprises a general injection element which defines at least two of the nut, the piston rod and the driver.

DESCRIPTION OF THE DRAWINGS

The invention will now be described with reference to the figures in which:

FIGS. 1a-1g discloses steps of an injection process according to an injection device according to a first embodiment, FIGS. 2a-7b discloses steps of an injection process according to an injection device according to a second embodiment, FIGS. 8-9e discloses elements of the injection device according to the second embodiment, and FIGS. 10a-10b discloses the general principles of the injection devices according to the first and the second embodiment.

FIGS. 1a-1g discloses an automatic injection device 100 comprising an ampoule holder 102, an ampoule 104, a piston 106, a resilient element in the form of a spring 108. The piston 106 is slidably arranged in the ampoule 104 and a reservoir 110 is defined by the ampoule 104 and the piston 106. In the initial configuration, when the device is delivered to the user/patient, the piston 106 is positioned in a proximal position relative to the ampoule holder 102, as shown in FIGS. 1a-d. By moving the piston 106 in the distal direction relative to the ampoule 104, a medicament contained in the reservoir 110 may be expelled through a needle 112, when said needle is fluidly connected to the ampoule as shown in FIGS. 1d-g.

Figures 4A, 4B:
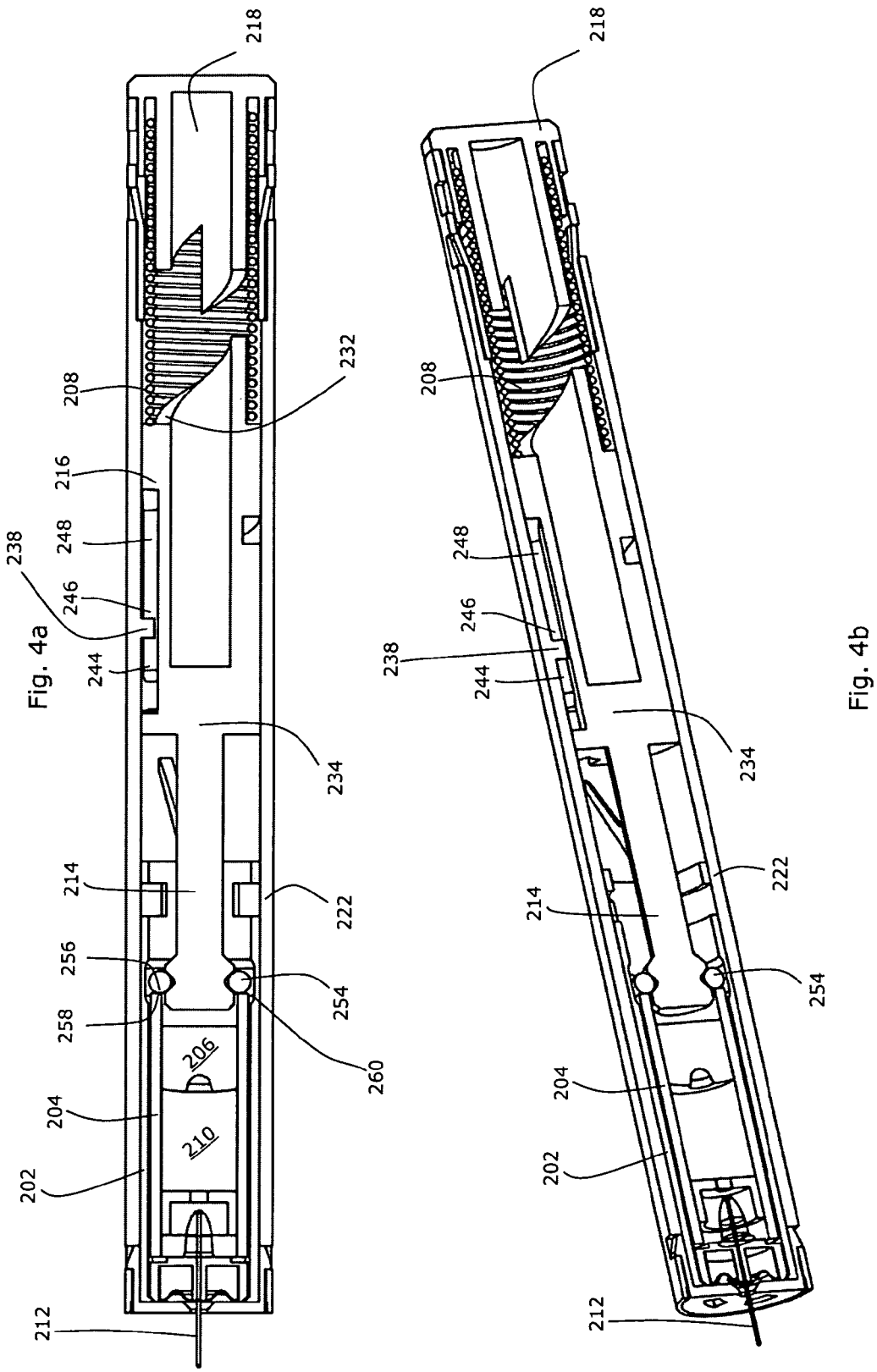

It may be seen from FIGS. 1e-1g (and 6a-7b) that no reservoir 110 is defined by the piston 106 and the ampoule 104, when the piston is positioned in its most distal position relative to the ampoule.

In order to advance the piston 106 in the distal direction a piston rod 114 is threadedly received in the piston holder 102 by engagement between a threaded inner surface of a passage defined in the ampoule holder 102 and the threaded outer surface of the piston rod 114. Accordingly, rotation of the piston rod in a clockwise direction relative to the ampoule holder—when sees from the proximal end towards the distal end—causes the piston rod to be moved in the distal direction. In order to rotate the piston rod 114 relative to the ampoule holder 102, the injection device comprises a driver 116 comprising a distal part 116' and a proximal part 116". The driver 116 is locked for rotation relative to the piston rod 114 prior to and during ejection of a dose of a medicament, i.e. in FIGS. 1a-1e. During retraction of the ampoule holder 102 from the deployed position (shown in FIG. 1d-f) by movement of the ampoule holder 102 in the proximal direction, the piston rod 114 is not locked for rotation relative to the driver 116.

The proximal part 116" of the driver 116 is coupled to a distal end 108' of the spring 108, while a proximal end 108'" of the spring 108 is coupled to an injection button 118, as may be seen in FIG. 1a. In the initial configuration the spring 108 is pre-strained rotationally and translationally. In order to maintain the spring in the pre-strained configuration, a locking arrangement 120 is provided by means of engagement between the injection button 118 and the proximal part 116" of the driver 116. When the user pushes the injection button 118 in the distal direction, the locking arrangement 120 disengages (as shown in FIG. 1c), and, thus, allows the spring to be partly unstrained in the translational direction. The injection button 118 is shown in its most proximal position in FIG. 1a and in its most distal position (i.e. when the user has moved the button in the distal direction) in FIG. 1b-g.

By unlocking the locking arrangement, the translationally strained spring 108 causes the driver to move in the distal direction as shown in FIGS. 1c-d. In order to prevent the rotationally strained spring from rotating the piston rod, the driver 116—which is coupled to the piston rod—is locked for rotation relative to the housing 122 in a first zone due to the tongue-groove arrangement 124. When the driver is moved out of said first zone (as illustrated in FIG. 1d) the tongue-groove arrangement 124 disengages and allows the driver 116 to rotate relative to the housing 122 as is explained in further detail below.

Movement of the driver through the first zone, i.e. from its initial position and into the position wherein the driver 116 may rotate relative to the housing 122, causes a proximal end of the needle 112 to perforate a piercable septum provided in the distal end of the ampoule 104 and subsequently advance the needle 112, the ampoule 104 and ampoule holder 102 in the distal direction, such that the distal end of the needle 112 may be inserted into the tissue of the user. In this position the driver 116 is free to rotate relative to the housing 122, whereby the rotationally strained spring 108 causes the driver 116 to rotate the piston rod 114 relative to the ampoule holder 102. Said rotation causes the piston rod 114 to be advanced in the distal direction, whereby the reservoir 110 is emptied—by ejection of the medicament contained therein—through the needle 112 due to the piston 106 being moved in the distal direction by the piston rod 114. During said rotational and translational movement of the piston rod 114, the driver 116 is moved rotationally and translationally relative to the housing due a threaded engagement 126 between the driver 116 and the housing 124, which is illustrated in FIGS. 1d-e.

The threaded engagement 126 is disengaged in the step from FIG. 1e to the step of FIG. 1f due to the translationally strained spring 108. At the same time, the driver 116 engages a nut 128, which is threadedly received in the housing 122, whereby the rotationally strained spring 108 causes the nut 128 to rotate in the clockwise direction, when sees from the proximal end towards the distal end. However as the orientation of the thread between the housing 122 and the nut 128 is reversed relative to the thread between the piston rod and the ampoule housing, clockwise rotation of the nut causes the nut 128 to move the ampoule holder 102 in the proximal direction, whereby the needle 112 is retracted from the tissue of the user, as shown in FIG. 1g.

FIGS. 2a-7b disclose steps in an injection process carried out by means of an automatic injection device 200 according to the second embodiment. The device 200 comprises an ampoule holder 202, an ampoule 204, a piston 206 and a resilient element in the form of a spring 208. A reservoir 210 is defined by the piston 206 and the ampoule 204. The piston 206 is slidingly received in the ampoule 204 such that movement of the piston 206 in the distal direction (i.e. to the left in the figure) causes a medicament contained in the reservoir 210 to be expelled through the needle 212.

In contrast to the embodiment of FIGS. 1a-1g, the device of FIGS. 2a-7b comprises a general injection element 234 (disclosed in further detail in FIGS. 9a-9e) which defines a piston rod portion 214, a driver portion 216 and the second inclined surfaces 232. The driver portion 216 defines a groove 236 which is adapted to receive a protrusion/tongue 238. The relative position between the groove 236 and the protrusion 238 are determining for the operation of the device 200. The groove 236 comprises a plurality of groove parts namely:

an insertion groove part 240,
an unlocking groove part 242,
a needle advancement groove part 244,
a decoupling groove part 246,
an injection groove part 248, and
a needle retraction groove part 250.

The groove parts 236, 240, 242, 244, 246, 248, 250 are illustrated stylistically in FIG. 10b and are described in further detail below.

It will be understood that the needle advancement groove part 244, the decoupling groove part 246 and a part of the injection groove part 248 are defined by different parts the longitudinally extending part of the groove 236.

In the below description of the use of the device, the protrusion 238 will be described as moving in the groove 236. However, it will be appreciated that as the housing during use remains in the same position relative to the hand of the user, the protrusion 238 also remains in the same position relative to the hand of the user. Thus relative to the hand of the user, it is rather the groove 236 and the general injection element 234 which moves, and thus causes the protrusion 238 to be positioned at different positions of the groove 236.

The insertion groove part 240 is provided so as to allow the protrusion 238 to be received in the groove 236 during manufacture.

FIGS. 2a and 2b discloses the device 200 in its initial position i.e. in the state in which the device 200 is delivered to a user. In the initial position, the needle 212 and the piston 206 are positioned in their most proximal position.

A user initiates the injection process by pushing the injection button 218 in the distal direction (to the left in the drawing), whereby a first inclined surface 230 of the injector button 218 is moved into contact with a second inclined surface 232 of the general injection element 234. Upon further movement of the injection button 218, the engagement between the inclined surfaces 230, 232 and the force from the injection button 218 causes the general injection element 234 to be rotated relative to the housing 222. During this movement, the protrusion 238 is moved in the unlocking groove part 242 (i.e. from the transition between the insertion groove part 240 and the unlocking groove part 242 to the transition between the unlocking groove part 242 and the needle advancement groove part 244). When the protrusion 238 has reached the end of the unlocking groove part 242 (as is illustrated in FIGS. 3a and 3b), the translationally prestrained spring 208 is free to force the general injection element 234 translationally in the distal direction, thus causing the protrusion 238 to be moved in the needle advancement groove part 244.

During the movement of the protrusion 238 in the needle advancement groove part 244, the general injection element 234 causes the ampoule holder 202 to be moved in the distal direction whereby the distally extending part of the needle 212 is inserted into the skin of the user and the proximal extending part of the needle 212 is inserted into the ampoule 204. The general injection element 234 defines a circumferentially extending outer groove 252 which is adapted to receive an O-ring 254. During advancement of the needle 212, a distally facing surface 256 of the O-ring abut a proximal facing end surface 258 of the ampoule holder 202, whereby advancement of the general injection element 234 in the distal direction causes the ampoule holder 202 to be moved in the distal direction. This causes the needle ends to be inserted into the user and the ampoule 204 as described above and is illustrated in FIGS. 4a and 4b.

When the needle 212 has been inserted, the O-ring 254 is positioned in the area of a circumferentially extending inner groove 260. In this position, the O-ring 254 is free to expand into the circumferentially extending inner groove 260. This allows the piston rod portion 214 to be moved into the ampoule, as the O-ring 254 disengages the groove 252. Upon further movement, the distally facing end surface of the piston rod portion 214 is brought into engagement with the proximal end surface of the piston 206. During the latter movement, the protrusion 238 is moved in the decoupling groove part 246 of the groove 236.

Further movement of the general injection element 234 causes the piston 206 to be moved in the distal direction whereby the medicament is expelled. During the latter movement, the protrusion 238 is moved in the injection groove part 248. It will be appreciated that the injection groove part 248 comprises a linear and a curved groove part, see especially FIG. 10b. When the protrusion is moved in the latter (curved) groove part, a first part of the medicament is expelled, while a second part of the medicament is expelled, when the protrusion 238 is moved in the linear/longitudinal groove part. With the latter terminology, the second part of the medicament is expelled before the first part of the medicament.

Movement in the linear/longitudinal groove part of the injection groove part 248 is caused by the spring 208 being prestrained translationally, while the movement in the curved groove part is caused by the spring 208 being prestrained rotationally.

When the medicament has been expelled, the general injection element 234 is positioned as illustrated in FIGS. 6a and 6b. In this position, the male snap lock element 262 extending from the piston rod portion 214 is allowed to snap into the female snap lock element 264. This causes the general injection element 234 to be locked for translational movement in the proximal direction relative to the ampoule holder 202.

Due to the rotationally strained spring 208, the protrusion continues its motion from the curved part of the injection groove part 248 and into the needle retraction groove part 250. Movement in the needle retraction groove part 250 causes the general injection element 234 to be moved in the proximal direction. As the latter movement is caused by the rotationally strained spring 208, it will be appreciated that at this stage of the injection process (i.e. a stage at which the spring has already been at least partly unstrained translationally), the rotational strain must be sufficiently large to overcome the remaining translational straining of the spring.

Figure 7A:
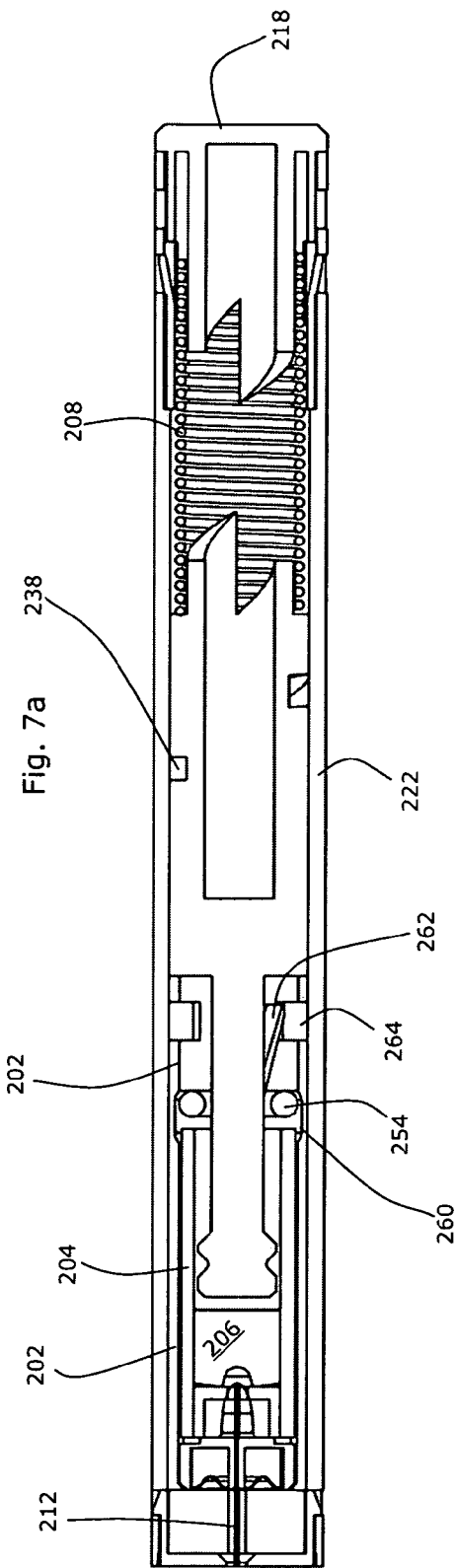
Figure 7B:
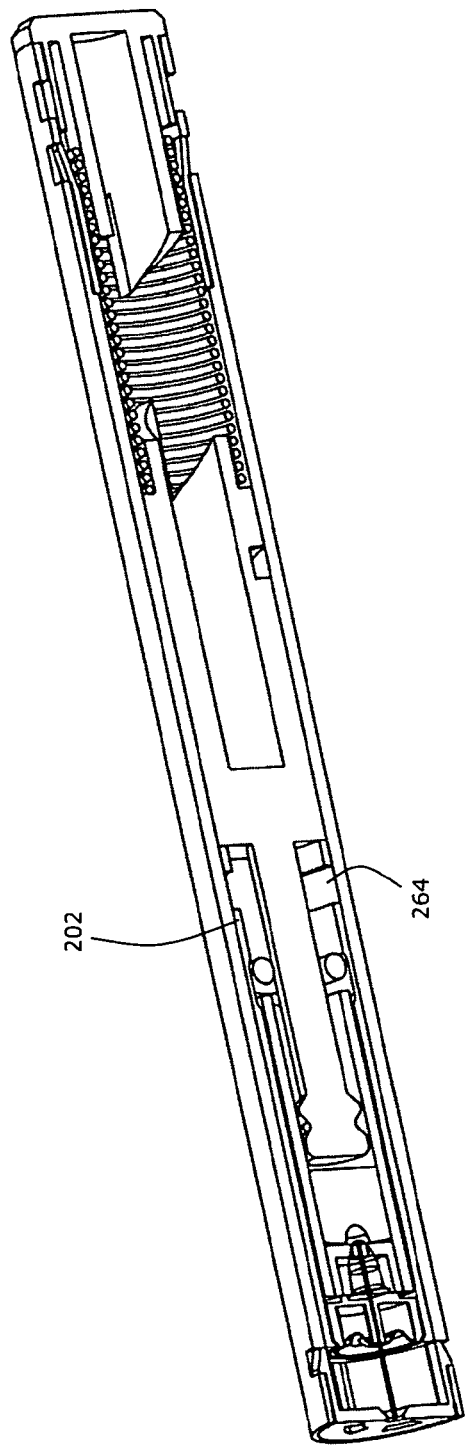

Movement of the general injection element 234 in the proximal direction causes the ampoule holder 202 to be moved in the proximal direction due to the snap lock arrangement 262, 264. This movement causes the needle 212 to be retraced from the skin of the user as the needle additionally is moved in the proximal direction. The needle in its fully retracted stage is illustrated in FIGS. 7a and 7b.

Figure 8:
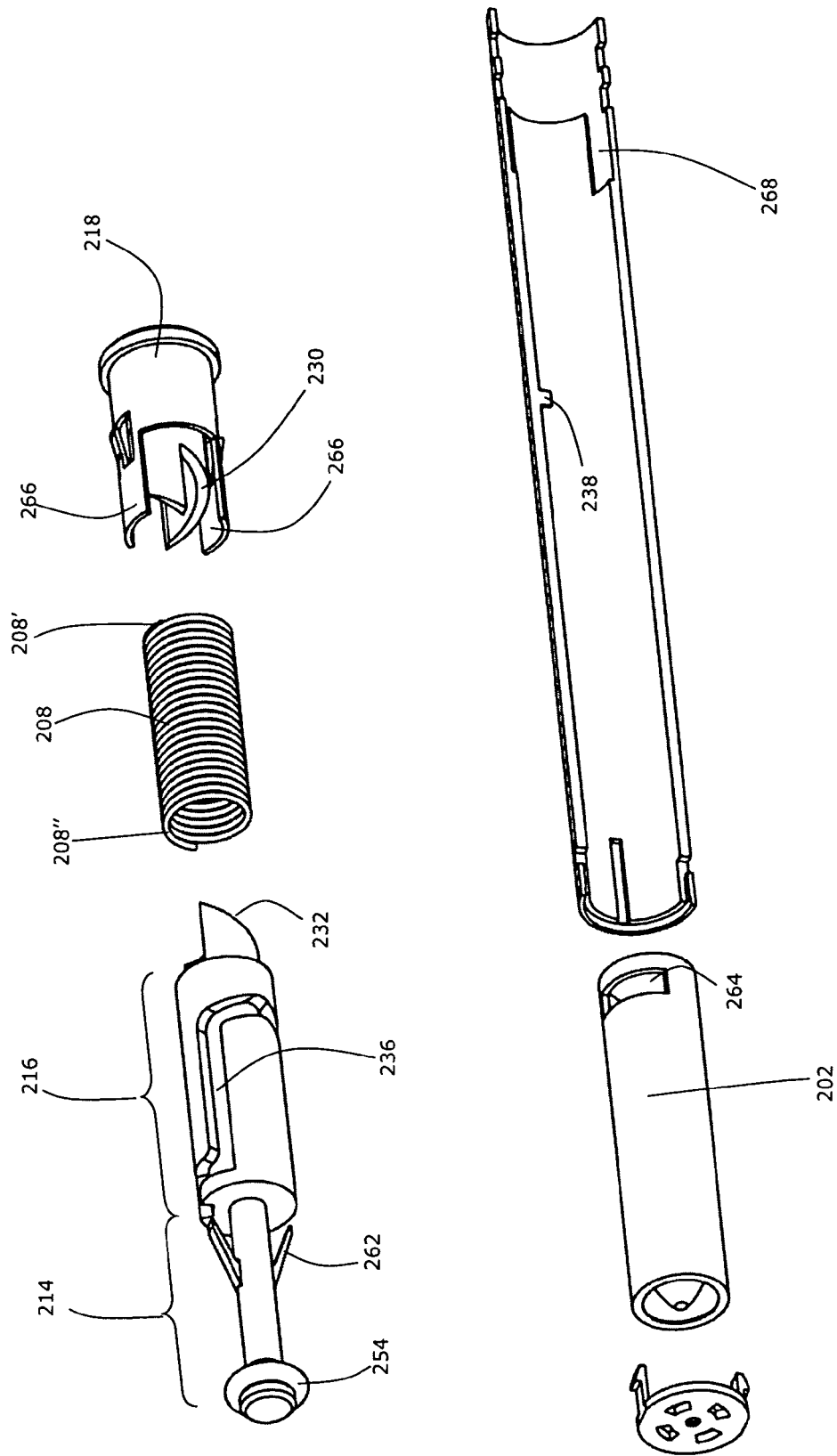

The elements of the injection device according to the second embodiment are illustrated in FIG. 8. The device comprises a injection button 218 defining tongues 266 adapted to be received in grooves 268 of the housing, so as to lock the injection button 218 for rotation relative to the housing. The injection button comprises first inclined surfaces 230 adapted to engage corresponding second inclined surfaces 232 of the general injection element 234. A spring 208 is fastened to the injection button 208 at a proximal end 208' and to the general injection element 234 at a distal end 208". The housing 222 comprises a protrusion 238 adapted to be received in the groove 236 which comprises a plurality of groove parts as is described previously.

FIG. 9a-9c discloses the general injection element 234 and is described in the aforementioned.

Figure 10A:
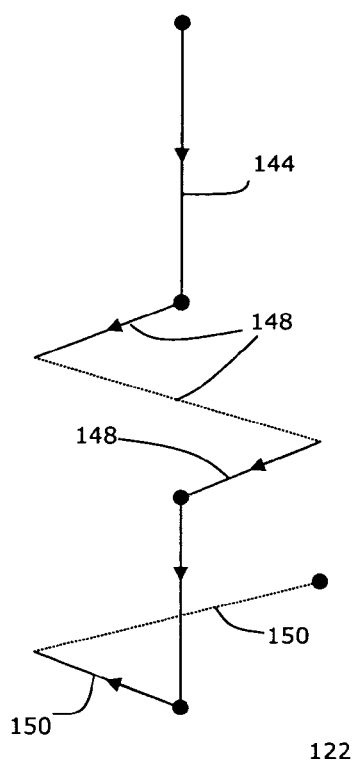
Figure 10B:
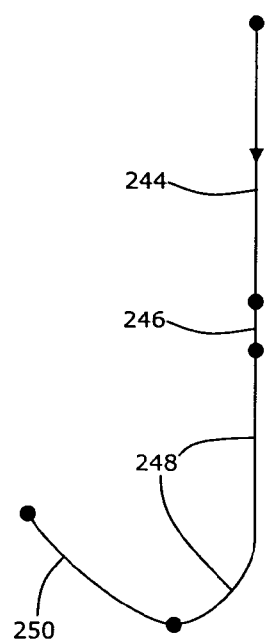

FIGS. 10a and 10b stylistically illustrate the principle of the first and the second embodiment, respectively. Although some of the reference numbers designate physical characteristics such as groove parts of the devices, the same reference numbers are used in FIGS. 10a and 10b to illustrate the rotational and/or translational movements during operation of the devices.

In both embodiments, the needle is inserted into the skin of the user by a translational movement—indicated by references 144 and 244. In the first embodiment (FIG. 10a), the driver 116 causes the ampoule holder 102 (and thus also the needle 112) to be moved translationally in the distal direction. In the second embodiment the general injection element 234 causes the ampoule holder 202 (and thus also the needle 212) to be moved translationally in the distal direction.

In both embodiments, at least a part of the medicament is expelled by rotating an element of the device. In the first embodiment (FIG. 10a), the piston rod 114 is rotated in order to expel the medicament. In the second embodiment (FIG. 10b), the general injection element 234 is initially moved translationally and subsequently rotationally so as to expel the medicament. In both cases the ejection process is terminated by rotation. The advantage of terminating the ejection process by rotation is that the ejection process is made more precise as the path travelled (by the piston rod 114 and the general injection element 234) is made longer whereby the effect of tolerances of any numerical size are minimised as such tolerances constitutes smaller fragment of the total travelled path.

Moreover in both embodiments, the needle 112, 212 is retracted by rotating an element of the device. In the first embodiment, the nut 128 is rotated, whereas in the second embodiment, the general injection element 234 is rotated.

The invention claimed is:

1. An automatic injection device comprising:
   a housing;
   an ampoule holder for accommodation of an ampoule having a piston slidably arranged therein, the ampoule and the piston defining a reservoir for accommodation of a medicament;
   a piston rod arranged such with respect to the ampoule holder that for a first set of relative positions between the ampoule holder and the piston rod, rotation of the piston rod causes the piston to be moved in a distal direction relative to the ampoule holder whereby a first part of the medicament is expelled; a resilient element adapted to:
   move the ampoule holder into a deployed position by moving the ampoule holder in the distal direction relative to the housing, and subsequently
   rotate the piston rod relative to the ampoule holder when the ampoule holder and the piston rod are positioned in the first set of relative positions whereby the first part of the medicament is expelled from the ampoule; and
   a means for retracting the ampoule holder away from the deployed position by cooperating with the resilient element to move the ampoule holder in a proximal direction relative to the housing.

2. An automatic injection device according to claim 1, wherein the resilient element subsequent to moving the ampoule holder into the deployed position and prior to rotating the piston rod, is adapted to move the piston rod translationally in the distal direction whereby a second part of the medicament is expelled.

3. An automatic injection device according to claim 1, wherein the piston rod is threadedly received in the ampoule holder.

4. An automatic injection device according to claim 1, wherein the means for retracting comprises a nut, wherein the ampoule holder when positioned in deployed position is rotationally and translationally locked relative to the nut which is arranged such with respect to the housing that rotation of the nut relative to the housing causes the nut and the ampoule holder to be moved in the proximal direction relative to the housing.

5. An automatic injection device according to claim 4, wherein the nut is threadedly connected to the housing.

6. An automatic injection device according to claim 4, further comprising a general injection element which defines both the nut and the piston rod.

7. An automatic injection device according to claim 1, wherein the resilient element comprises a torsion spring.

8. An automatic injection device according to claim 7, further comprising a driver which is coupled to a distal end of the spring, whereby rotational unstraining of the spring causes the driver to rotate.

9. An automatic injection device according to claim 8, wherein the means for retracting comprises the driver and a nut wherein, when the ampoule holder is positioned in the deployed position and subsequent to expelling of medicament from the ampoule, the driver engages the nut so that rotation of the driver causes rotation of the nut, the nut being arranged with respect to the housing such that rotation of the nut relative to the housing causes the nut to move the ampoule holder in the proximal direction relative to the housing.

10. An automatic injection device according to claim 9, wherein the nut is threadedly received in the housing and wherein rotation of the nut relative to the housing causes the nut and the ampoule holder to be moved in the proximal direction relative to the housing.

11. An automatic injection device according to claim 7 wherein the spring is prestrained rotationally and translationally.

12. An automatic injection device according to claim 8, wherein a proximal end of the spring is coupled to an injection button for initiating the injection process and wherein the driver during said injection process is locked for rotation relative to the piston rod such that rotation of the driver causes the piston rod to rotate.

13. An automatic injection device according to claim 8, wherein the driver is displaceable between a proximal and a distal position relative to the housing, and wherein the driver is rotatable relative to the housing when positioned in the distal position and locked for rotation relative to the housing in a zone extending from the proximal position and towards the distal position.

14. An automatic injection device according to claim 8, wherein the spring is prestrained translationally and rotationally and arranged such that upon movement of the injection button in the distal direction, the spring forces the driver translationally from the proximal position into the distal position in which the rotationally prestrained spring causes the driver to rotate the piston rod.

15. An automatic injection device according to claim 8, wherein the driver and the piston rod forms a general injection element, wherein the means for retracting comprises a protrusion in the housing and a groove on the driver, wherein the protrusion adapted to be received in the groove of the driver such that the relative position between the groove and the protrusion are determining for the operation of the automatic injection device.

16. An automatic injection device according to claim 15, wherein the groove comprises:
   an insertion groove part,
   an unlocking groove part,
   a needle advancement groove part,
   a decoupling groove part,
   an injection groove part, and
   a needle retraction groove part.

17. An automatic injection device according to claim 1, further comprising a needle arranged such that upon movement of the ampoule holder into the deployed position, a proximal end of the needle penetrates a septum of the ampoule and subsequently a distal end of the needle penetrates the skin of a user.

18. An automatic injection device according to claim 1, further comprising a needle arranged such that upon movement of the ampoule holder into the deployed position, a distal end of the needle penetrates the skin of a user and subsequently a proximal end of the needle penetrates a septum of the ampoule.

* * * * *